United States Patent [19]

Misaki et al.

[11] 4,390,702

[45] Jun. 28, 1983

[54] 3-SUBSTITUTED-3-FLUOROPYRUVIC ACIDS AND THEIR ESTERS AND SALTS, AND PRODUCTION THEREOF

[75] Inventors: Susumu Misaki; Masahiro Suefuji; Tadahiko Tsushima; Hiroshi Tanida, all of Osaka, Japan

[73] Assignees: Daikan Kogyo Co., Ltd.; Shionogi and Co., Ltd., both of Osaka, Japan

[21] Appl. No.: 220,917

[22] Filed: Dec. 29, 1980

[30] Foreign Application Priority Data

Dec. 29, 1979 [JP] Japan ................................ 54-173593

[51] Int. Cl.³ .................... C07D 213/55; C07C 69/76; C07C 53/21
[52] U.S. Cl. .................................. 546/296; 546/298; 546/300; 546/301; 546/302; 546/304; 546/307; 546/310; 546/311; 546/312; 546/314; 546/315; 546/341; 560/23; 560/51; 560/174; 562/434; 562/437; 562/438; 562/459; 562/577
[58] Field of Search .......................... 560/174, 23, 51; 562/577, 574, 434, 437, 438, 459; 546/341, 314, 315, 296, 298, 300, 301, 302, 304, 307, 310, 311, 312

[56] References Cited

U.S. PATENT DOCUMENTS

3,972,921  8/1976  Dolling et al. .................... 562/574

OTHER PUBLICATIONS

Blank et al., J. Chem. Soc., 2190 (1955).
Nair et al., J. Org. Chem., 23, 137 (1958).

*Primary Examiner*—Alan L. Rotman
*Attorney, Agent, or Firm*—Birch, Stewart, Kolasch & Birch

[57] ABSTRACT

A 3-substituted-3-fluoropyruvic acid and its ester and salt of the formula:

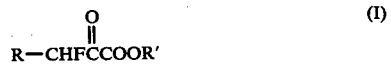

wherein R is a lower alkyl group, a lower alkanoyl group, a fluorinated lower alkanoyl group, a substituted or unsubstituted phenyl group or a substituted or unsubstituted pyridyl group and R' is a hydrogen atom, an ester-forming residue or a salt-forming residue, and their production.

10 Claims, No Drawings

3-SUBSTITUTED-3-FLUOROPYRUVIC ACIDS AND THEIR ESTERS AND SALTS, AND PRODUCTION THEREOF

The present invention relates to novel 3-substituted-3-fluoropyruvic acids and their esters and salts, and production thereof.

The 3-substituted-3-fluoropyruvic acids and their esters and salts of the present invention are the compounds of the formula:

wherein R is a lower alkyl group, a lower alkanoyl group, a fluorinated lower alkanoyl group, a substituted or unsubstituted phenyl group or a substituted or unsubstituted pyridyl group and R' is a hydrogen atom, an ester-forming residue or a salt-forming residue. As the ester-forming residue, there may be exemplified lower alkyl, substituted or unsubstituted phenyl, etc. Examples of the salt-forming residue are alkali metal (e.g. sodium, potassium), alkaline earth metal (e.g. calcium, barium), ammonium, lower alkylammonium, etc.

In the above meanings, the term "substituted or unsubstituted phenyl" covers a phenyl group substituted or unsubstituted with one or two of lower alkyl, lower alkoxy, lower alkanoyl, hydroxyl, nitro, amino, mino(-lower)alkylamino, di(lower)alkylamino, etc. Likewise, the term "substituted or unsubstituted pyridyl" covers a pyridyl group substituted or unsubstituted with one or two of lower alkyl, lower alkoxy, lower alkanoyl, hydroxyl, nitro, amino, mono(lower)alkylamino, di(lower)alkylamino, etc.

Throughout the specification, the term "lower" is intended to mean a group having not more than 8 carbon atoms, particularly not more than 5 carbon atoms. Thus, examples of lower alkyl are methyl, ethyl, propyl, isopropyl, butyl, isobutyl, t-butyl, etc.; examples of lower alkoxy are methoxy, ethoxy, propoxy, isopropoxy, butoxy, isobutoxy, t-butoxy, etc.; examples of lower alkanoyl are formyl, acetyl, propionyl, butyryl, isobutyryl, valeryl, etc.; examples of lower alkylamino are methylamino, ethylamino, propylamino, etc.; and examples of di(lower)alkylamino are dimethylamino, methylethylamino, dibutylamino, etc.

Of the 3-substituted-3-fluoropyruvic acids and their esters and salts representable by the formula (I), typical examples are 3-methyl-3-fluoropyruvic acid, 3-butyryl-3-fluoropyruvic acid, 3-phenyl-3-fluoropyruvic acid, 3-(4-chlorophenyl)-3-fluoropyruvic acid, 3-(2-nitrophenyl)-3-fluoropyruvic acid, etc., and their esters and salts.

Introduction of a fluorine atom(s) into the molecules of organic compounds can afford physiologically active substances. For realization of such introduction, there have been proposed various methods, of which typical examples are the one with Schiemann reaction, the one by halogen substitution, the one using special fluorinating agents (e.g. perfluoroalkyl hypofluorite, polyfluorinated metal, Yarovenko reagent, sulfur tetrafluoride), the one with fluorine gas, etc. Among them, the method with fluorine gas is defective in being non-selective on the position to be fluorinated and difficult in regulation of the reaction conditions, because of the drastic progress of fluorination. In recent years, it was reported that the use of fluorine gas in a dilute form with any inert gas in an inert solvent such as a halogenated hydrocarbon under cooling can overcome the said defects [S. Nagase: "Yuki Gosei Kagaku Kyokai Shi" (Journal of the Association of Organic Synthetic Chemistry), Vol. 31, page 441 (1973)]. However, the effective application of this improvement is still restricted to some certain cases (e.g. Japanese Patent Publication No. 3875/1979).

As the result of an extensive study for further development of the direct fluorination with fluorine gas or any other fluorinating agent, it has now been found that 3-substituted-pyruvic esters can be fluorinated easily with a fluorinating agent to give the corresponding 3-substituted-3-fluoropyruvic esters in good yields. It is notable that the said monofluorination (i.e. initial fluorine-addition and subsequent dehydrofluorination) proceeds with a high selectivity. Because of the high selectivity and good yield, the above direct fluorination is quite applicable at an industrial scale.

According to the present invention, the 3-substituted-3-fluoropyruvic acids and their esters and salts of the formula (I) can be prepared by reacting a 3-R-pyruvic esteer of the formula:

wherein R" is an ester-forming residue and R is an defined above with a fluorinating agent to give a 3-R-3-fluoropyruvic ester of the formula:

wherein R and R" are each as defined above, optionally followed by hydrolysis of the 3-R-3-fluoropyruvic ester (III) to give a 3-R-3-fluoropyruvic acid of the formula:

wherein R is as defined above and further optionally followed by conversion of the 3-R-3-fluoropyruvic acid (IV) into its salt, i.e. a 3-R-3-fluoropyruvate of the formula:

wherein R'" is a salt-forming residue and R is as defined above.

Still, the salt-forming residue represented by R or R'" may be monovalent or polyvalent.

In the process of this invention, the fluorination of the 3-R-pyruvic ester (II) can usually proceed only when it takes an enol structure. Thus, it is presumed that the fluorination takes place after the 3-R-pyruvic ester (II) retains an enol structure in the reaction system.

The conversion of the 3-R-pyruvic ester (II) in a keto structure into the one in an enol structure may be achieved by any per se conventional procedure. For instance, the incorporation of a small amount of an alkali into the reaction system can attain such conversion. The presence of a basic solvent (e.g. diazabicyclononene) in the reaction system is particularly effective for this purpose.

As the florinating agent, there may be used fluorine gas, perfluoroalkyl hypofluorite, xenon difluoride, etc. It may be used as such or in a dilute form with any inert gas (e.g. nitrogen, argon).

The fluorination is practically carried out by introducing the fluorinating agent as such or in a dilute form into a reaction medium comprising the 3-R-pyruvic ester (II) and preferably an inert solvent at a temperature above the freezing point and below the boiling point of the inert solvent while stirring or under circulation. The introduction of the fluorinating agent may be made onto the surface of the reaction medium.

Examples of the inert solvent, which may be optionally employed, are halogenated hydrocarbons (e.g. chlorohydrocarbons, chlorofluorohydrocarbons, perfluorohydrocarbons), acetonitrile, glymes (e.g. diglyme, triglyme, tetraglyme), alkanoic acids (e.g. acetic acid, propionic acid), fluorinated alkanoic acids (e.g. fluoropropionic acid), alkanols (e.g. methanol, ethanol), fluorinated alkanols (e.g. trifluoroethanol), ethers (e.g. diethyl ether), fluorinated ethers (e.g. perfluoroalkyl ether), fluorinated ketones (e.g. hexafluoroacetone), perfluorodecalin, perfluorotributylamine, etc. Among them, the use of acetonitrile, glymes and halogenated hydrocarbons is particularly preferred. When the starting 3-R-pyruvic ester (II) is in a liquid form, the use of the above inert solvent is not essential.

Since the fluorination is an exothermic reaction, it is desirable to eliminate the heat generated in the reaction system by stirring the reaction mixture, whereby the reaction proceeds smoothly. The reaction temperature may be above the freezing point and below the boiling point of the inert solvent used, usually in a range of −20° to 20° C.

When desired, the reaction may be effected in the presence of a dehydrofluorinating agent so as to suppress the proceeding of side reactions. Examples of the dehydrofluorinating agent are molecular sieve, sodium fluoride, silica gel, etc.

As the reaction mode, there may be adopted either a batch system or a continuous circulation system with counter-current contact.

In order to attain a better yield of the desired fluorinated product, the conversion of the starting compound may be maintained in a certain range, for instance, from 50 to 60%. After separation and recovery of the fluorinated product from the reaction mixture, the remainder is again subjected to fluorination. By this procedure, production of the polymer-like by-product which causes the loss of the yield is remarkably reduced.

In case of R in the 3-R-pyruvic ester (II) being lower alkanoyl, it may be simultaneously fluorinated to give the 3-fluorinated alkanoyl-3-fluoropyruvic ester. Such case may be understood to fall within the scope of this invention, since the fluorination takes place anyhow at the 3-position.

Hydrolysis of the 3-R-3-fluoropyruvic ester (III) into the 3-R-3-fluoropyruvic acid (IV) and conversion of the 3-R-3-fluoropyruvic acid (IV) into the 3-R-3-fluoropyruvate (V) may be effected in per se conventional procedures well known to those skilled in the art.

The 3-substituted-3-fluoropyruvic acids and their esters and salts of the formula (I) can be utilized as intermediary compounds for synthetizing physiologically active substances. For instance, sodium 3-R-3-fluoropyruvate can be converted into 3-R-3-fluoro-2-aminopropionic acid, which is per se useful as an antimicrobial agent, by reductive amination as shown below:

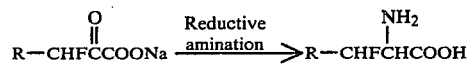

wherein R is as defined above.

Practical and preferred embodiments of the present invention are illustratively shown in the following Examples.

EXAMPLE 1

Ethyl 3-phenylpyruvate (10 g; 0.052 mol) is dissolved in a mixture of acetonitrile (60 g) and trichlorotrifluoroethane (410 g), and the resulting solution is cooled to −10° C. Then, fluorine gas (0.067 mol) diluted with nitrogen to 10% concentration is introduced therein over a period of 2.5 hours while stirring vigorously. After addition of sodium fluoride (2 g), the solvent is distilled off under reduced pressure, and the residue is rectified to give ethyl 3-phenyl-3-fluoropyruvate (4.37 g). Boiling point, 90°–95° C./1 mmHg.

Elementary analysis: Calcd.: C, 61.58%; H, 5.24%; F, 9.05%. Found: C, 61.18%; H, 5.23%, F, 9.00%.

Mass spectrum: m/e=210 (M$^+$), 182 (M$^+$—CO), 162 (M$^+$—CO—HF), 109 (C$_7$H$_6$F), 29 (C$_2$H$_5$).

Infrared absorption spectrum (film): 3500 (w), 2980 (m), 1750 (s), 1490 (w), 1450 (m), 1370 (w), 1250–1280 (s), 1090 (w), 1020 (m), 760 (m), 690 (m) cm$^{-1}$.

EXAMPLE 2

In the same manner as in Example 1, methyl 3-phenylpyruvate (35.62 g; 0.2 mol) is dissolved in a mixture of acetonitrile (240 g) and trichlorotrifluoroethane (1.6 L) and reacted with fluorine at −10° C. After the same work-up as in Example 1, the residue is rectified to give methyl 3-phenyl-3-fluoropyruvate (11.8 g). The silyl enol ether obtained by the treatment of the above product with bis-(trimethylsilyl)acetamide (BSA) in methylene chloride shows boiling point 93°–95° C./1 mmHg and $^{19}$F NMR (CDCl$_3$), δ (int. C$_6$F$_6$)+31.5 (s).

EXAMPLE 3

In the same manner as in Example 1, methyl 3-(4-chlorophenyl)pyruvate is dissolved in acetonitrile (500 ml) and reacted with fluorine at −10° C. After the same work-up as in Example 1, the resulting crude product is rectified to give syrupy methyl 3-(4-chlorophenyl)-3-fluoropyruvate (7.49 g).

Elementary analysis: Calcd.: C, 52.06%; H, 3.47%; F, 8.24%. Found: C, 51.81%; H, 3.40%; F, 8.21%.

Infrared absorption spectrum (film): 3000 (w), 1750–1740 (s), 1600 (m), 1500 (m), 1440 (m), 1417 (m), 1260 (s), 1090 (m), 1040–1020 (m), 860 (m), 820 (m), 790 (m), 750 (m) cm$^{-1}$.

The silyl enol ether prepared by the treatment of the product with BSA in methylene chloride shows boiling point 130°–132° C./1 mmHg and $^{19}$F NMR (CDCl$_3$), δ (int. C$_6$F$_6$)+29.8 (s).

EXAMPLE 4

In the same manner as described in Example 1, ethyl 3-(4-nitrophenyl)pyruvate (11.86 g) is dissolved in acetonitrile (500 ml) and reacted with fluorine at −10° C. After the same work-up as above described, the residue is rectified to give syrupy ethyl 3-(4-nitrophenyl)-3-fluoropyruvate (3.83 g).

Elementary analysis: Calcd.: C, 51.76%; H, 3.92%; N, 5.49%; F, 7.49%. Found: C, 51.53%; H, 3.80%; N, 5.53%; F, 7.25%.

Infrared absorption spectrum (film): 3000 (w), 1750–1740 (s), 1615 (m), 1530 (s), 1350 (s), 1260 (s), 1140–1100 (s), 1040–1020 (s), 860 (m), 840 (m) cm$^{-1}$.

The silyl enol ether prepared by the treatment of the product with BSA in the same manner as above described shows boiling point 120° C./0.05–0.08 mmHg and $^{19}$F NMR (CDCl$_3$), δ (int. C$_6$F$_6$)+26.2 (s).

EXAMPLE 5

In the same manner as in Example 1, ethyl 3-butyryl-pyruvate (9.53 g; 0.0512 mol) is dissolved in acetonitrile (94 g) and reacted with fluorine at −5° C. By distilling off the solvent under reduced pressure, there is obtained a crude product (5.5 g), which is rectified to give ethyl 3-butyryl-3-fluoropyruvate. Boiling point, 72°–78° C./2 mmHg.

Mass spectrum: m/e=222 (M+), 174 (M+—CO—HF), 131 (M+—COOC$_2$H$_5$), 71 (C$_4$H$_7$O), 29 (C$_2$H$_5$).

Infrared absorption spectrum (CHCl$_3$): 3500 (w), 2950 (m), 1730 (s), 1650 (m), 1585 (m), 1460 (m), 1368 (m), 1260–1200 (s), 1010 (m), 860 (m).

$^{19}$FNMR (CDCl$_3$), δ (int. C$_6$F$_6$)−34.2 (dt, $J_{HFgem}$=49.0 Hz, $J_{F\text{-}CH_2CH_2CH_3}$=3.0 Hz),+3.0 (t, $J_{F\text{-}CH_2CH_2CH_3}$=3.0 Hz),+47.3 (s).

EXAMPLE 6

In the same manner as in Example 1, methyl 3-(2-nitrophenyl)pyruvate (2.23 g; 10 mmol) is dissolved in acetonitrile (50 g) and reacted with fluorine. By distilling off the solvent under reduced pressure, there is obtained a crude product, whicch is rectified to give methyl 3-(2-nitrophenyl)-3-fluoropyruvate.

Mass spectrum: m/e=241 (M+), 216 (M+—O—F), 182 (M+—COOCH$_3$), 154 (C$_7$H$_5$FNO$_2$), 15 (CH$_3$).

EXAMPLE 7

In the same manner as in Example 1, ethyl 3-methyl-pyruvate (1.0 g; 8.62 mmol) is dissolved in acetonitrile (22.5 g) and reacted with fluorine. By distilling off the solvent under reduced pressure, there is obtained a crude product, which is rectified to give ethyl 3-methyl-3-fluoropyruvate.

Identification of the product is made by infrared absorption spectrum and mass spectrum.

EXAMPLE 8

To the crude product of ethyl 3-phenyl-3-fluoropyruvate (10.6 g) obtained in Example 1, a 50% aqueous solution of isopropanol (300 ml) is added, and sodium bicarbonate (9.0 g) is added thereto. The mixture is heated gradually while stirring, and hydrolysis is effected at 50° C. for 15 hours. Thereafter, water-insoluble substances are extracted with ethyl acetate (70 ml each for three times). Then, the water layer is admixed with ethyl acetate (200 ml) and made acidic (pH, 1.0–2.0) with 1 N hydrochloric acid under ice cooling. The ethyl acetate layer is dried over magnesium sulfate and distilled under reduced pressure to give 3-phenyl-3-fluoropyruvic acid (6.3 g) as an oil.

$^{19}$FNMR (CD$_3$OD), δ (ext. CF$_3$COOH) −31.8 (s)
$^{1}$HNMR (CD$_3$OD), δ 8.20–6.80 (m, 5H ArH).

The resulting acid is neutralized with an aqueous solution of sodium hydroxide and concentrated under reduced pressure to dryness to give the corresponding sodium salt, i.e. sodium 3-phenyl-3-fluoropyruvate.

What is claimed is:

1. A process for preparing a 3-substituted-3-fluoropyruvic acid or ester or salt thereof of the formula:

wherein R is a lower alkyl group, a lower alkanoyl group, a monofluorinated lower alkanoyl group, a substituted phenyl group substituted with one or two groups selected from the group consisting of lower alkyl, lower alkoxy, lower alkanoyl, hydroxyl, halogeno, nitro, amino, mono(lower)alkylamino and di(lower)alkylamino groups an unsubstituted phenyl group, a substituted pyridyl group substituted with one or two groups selected from the group consisting of lower alkyl, lower alkoxy, lower alkanoyl, hydroxyl, nitro, amino, mono(lower)alkylamino and di(lower)alkylamino groups or an unsubstituted pyridyl group and R' is a hydrogen atom, an ester-forming residue selected from the group consisting of a lower alkyl group, a substituted phenyl group substituted with one or two groups selected from the group consisting of lower alkyl, lower alkoxy, lower alkanoyl, hydroxyl, halogeno, nitro, amino, mono(lower)alkylamino and di(lower)alkylamino groups, an unsubstituted phenyl group or a salt-forming residue selected from the group consisting of alkali metal, alkaline earth metal, ammonium and lower alkylammonium salts which comprises reacting a 3-R-pyruvic ester of the formula:

wherein R" is said ester-forming residue and R is as defined above with a fluorinating agent selected from the group consisting of fluorine, perfluoroalkyl hypofluorite and xenon difluoride in a solvent inert under the reaction conditions to give a 3-R-3-fluoropyruvic ester of the formula:

wherein R and R" are each as defined above, optionally followed by hydrolysis of the 3-R-3-fluoropyruvic ester (III) to give a 3-R-3-fluoropyruvic acid of the formula:

wherein R is as defined above and further optionally followed by conversion of the 3-R-3-fluoropyruvic acid (IV) into a salt thereof of the formula:

wherein R''' is said salt-forming residue and R is as defined above.

2. The process according to claim 1, wherein the fluorinating agent is fluorine gas.

3. The process according to claim 1, wherein the solvent is acetonitrile, a glyme or a halogenated hydrocarbon, or their mixture.

4. The process according to claim 1, wherein the fluorination is carried out at a temperature above the freezing point and below the boiling point of the solvent.

5. The process according to claim 2, wherein the fluorine gas is used in a dilute form with an inert gas.

6. The process according to claim 1, wherein the fluorination is carried out in the presence of a dehydrofluorinating agent.

7. The process according to claim 1, wherein the fluorination is carried out in the presence of a dehydrofluorinating agent selected from the group consisting of molecular sieve, sodium fluoride and silica gel.

8. The process according to claim 1, wherein the inert solvent is selected from the group consisting of halogenated hydrocarbons, acetonitrile, glymes, alkanoic acids, fluorinated alkanoic acids, alkanols, fluorinated alkanols, ethers, fluorinated ethers, fluorinated ketones, perfluorodecalin and perfluorotributylamine.

9. The process according to claim 1, wherein said 3-R-pyruvic ester (II) is selected from the group consisting of 3-phenylpyruvate, methyl 3-phenylpyruvate, methyl 3-(4-chlorophenyl)pyruvate, ethyl 3-(4-nitrophenyl)pyruvate, ethyl 3-butyrylpyruvate, methyl 3-(2-nitrophenyl)pyruvate, ethyl 3-methylpyruvate, and ethyl 3-phenyl-3-fluoropyruvate.

10. A 3-substituted-3-fluoropyruvic acid or ester or salt thereof of the formula:

$$R-CHFCCOOR' \quad (I)$$
$$\phantom{R-CHF}\|\phantom{COOR'}$$
$$\phantom{R-CHF}O$$

wherein R is a lower alkanoyl group, a substituted phenyl group substituted with one or two groups selected from the group consisting of halogeno and nitro or an unsubstituted phenyl group; and R' is a hydrogen atom, a lower alkyl group or an alkali metal salt-forming residue.

* * * * *